(12) United States Patent
Fritsch et al.

(10) Patent No.: US 11,808,732 B2
(45) Date of Patent: Nov. 7, 2023

(54) METHOD FOR MONITORING A GAS SENSOR

(71) Applicant: Robert Bosch GmbH, Stuttgart (DE)

(72) Inventors: Andreas Fritsch, Waiblingen (DE); Sabine Gräbe, Ludwigsburg (DE); Torsten Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 597 days.

(21) Appl. No.: 16/876,296

(22) Filed: May 18, 2020

(65) Prior Publication Data

US 2020/0363370 A1 Nov. 19, 2020

(30) Foreign Application Priority Data

May 17, 2019 (DE) .......................... 102019207251.8

(51) Int. Cl.
*G01N 27/416* (2006.01)
*G01N 33/00* (2006.01)
(Continued)

(52) U.S. Cl.
CPC ..... *G01N 27/4163* (2013.01); *B01D 53/9431* (2013.01); *F01N 11/00* (2013.01);
(Continued)

(58) Field of Classification Search
CPC ........ F01N 3/108; F01N 3/0842; F01N 3/029; F01N 3/0293; F01N 3/0814; F01N 3/0871; F01N 3/0885; F01N 3/206; F01N 3/2066; F01N 3/2073; F01N 3/208; F01N 11/00; F01N 11/002; F01N 11/005; F01N 11/007; F01N 2240/25; F01N 2240/34; F01N 2240/40; F01N 2550/00; F01N 2550/02;
(Continued)

(56) References Cited

U.S. PATENT DOCUMENTS

2010/0161242 A1* 6/2010 Wang ................. G01N 27/4074
702/24
2011/0016949 A1* 1/2011 Sasaki ................ G01N 27/4175
73/23.31
(Continued)

FOREIGN PATENT DOCUMENTS

DE 102010028543 11/2011
DE 102014213213 1/2015
JP 2014224504 12/2014

*Primary Examiner* — Binh Q Tran
(74) *Attorney, Agent, or Firm* — Michael Best & Friedrich LLP

(57) ABSTRACT

A method for monitoring a gas sensor (14) which comprises two electrochemical measuring cells (20, 30) and which is arranged in an exhaust tract (10) of an internal combustion engine (11), wherein the sensor elements (20, 30) exhibit a substantially identical sensitivity towards a first gas component and a different sensitivity towards a second gas component and are insensitive towards further gas components. In an operating state in which an exhaust gas stream at the gas sensor (14) contains less of the second gas component than of the first gas component a concentration of the first gas component is calculated from each of the sensor signals from the sensor elements (20, 30) and a defect in a sensor element (20, 30) is deduced from the concentrations of the first gas component.

9 Claims, 2 Drawing Sheets

(51) Int. Cl.
*B01D 53/94* (2006.01)
*F01N 11/00* (2006.01)
*G01N 27/407* (2006.01)
*F01N 3/08* (2006.01)
*F01N 3/20* (2006.01)

(52) U.S. Cl.
CPC ......... *G01N 27/407* (2013.01); *G01N 33/007* (2013.01); *G01N 33/0037* (2013.01); *G01N 33/0054* (2013.01); *F01N 3/0871* (2013.01); *F01N 3/0885* (2013.01); *F01N 3/2006* (2013.01); *F01N 3/206* (2013.01); *F01N 3/208* (2013.01); *F01N 3/2066* (2013.01); *F01N 3/2073* (2013.01); *F01N 11/007* (2013.01); *F01N 2240/25* (2013.01); *F01N 2550/02* (2013.01); *F01N 2550/03* (2013.01); *F01N 2560/02* (2013.01); *F01N 2560/021* (2013.01); *F01N 2560/026* (2013.01); *F01N 2570/18* (2013.01); *F01N 2610/02* (2013.01); *F01N 2610/102* (2013.01); *F01N 2610/1453* (2013.01); *F01N 2900/04* (2013.01); *F01N 2900/08* (2013.01); *F01N 2900/1614* (2013.01); *F01N 2900/1616* (2013.01)

(58) Field of Classification Search
CPC ............. F01N 2550/03; F01N 2560/00; F01N 2560/02; F01N 2560/021; F01N 2560/026; F01N 2570/18; F01N 2610/00; F01N 2610/01; F01N 2610/02; F01N 2610/03; F01N 2610/04; F01N 2610/05; F01N 2610/06; F01N 2610/102; F01N 2610/1453; F01N 2900/04; F01N 2900/08; F01N 2900/14; F01N 2900/1402; F01N 2900/1404; F01N 2900/1406; F01N 2900/1614; F01N 2900/18; F01N 2900/1806; F01N 2900/1616; B01D 53/9418; B01D 53/9431; B01D 53/9495; B01D 2251/2062; B01D 2251/2065; B01D 2251/2067; B01D 2257/40; B01D 2257/404; B01D 2257/406; Y02T 10/12; Y02T 10/40; Y02A 50/20; F02D 2041/1468; G01N 27/4163; G01N 27/407; G01N 27/4074; G01N 31/002; G01N 33/0037; G01N 33/0054; G01N 33/007

See application file for complete search history.

(56) References Cited

U.S. PATENT DOCUMENTS

| | | | |
|---|---|---|---|
| 2011/0106402 A1* | 5/2011 | Yasui | F01N 13/0097 |
| | | | 701/102 |
| 2012/0234077 A1 | 9/2012 | Wang et al. | |
| 2013/0139489 A1 | 6/2013 | Liu et al. | |
| 2015/0013431 A1 | 1/2015 | Kakimoto et al. | |
| 2016/0201541 A1* | 7/2016 | Matsumoto | F01N 11/007 |
| | | | 422/105 |
| 2016/0215669 A1* | 7/2016 | Matsumoto | F01N 3/0842 |
| 2016/0356195 A1* | 12/2016 | Hibino | F01N 3/208 |
| 2016/0356196 A1* | 12/2016 | Nakano | F01N 9/00 |
| 2017/0184536 A1* | 6/2017 | Kawamoto | G01N 27/4075 |
| 2018/0274428 A1* | 9/2018 | Nakamura | G01N 27/4175 |
| 2018/0283308 A1* | 10/2018 | Hayashita | F02D 41/1447 |
| 2019/0128166 A1* | 5/2019 | Nakagaki | F01N 11/007 |
| 2019/0203624 A1* | 7/2019 | Gong | F01N 3/035 |

* cited by examiner

METHOD FOR MONITORING A GAS SENSOR

BACKGROUND OF THE INVENTION

The present invention relates to a method for monitoring a gas sensor. The present invention further relates to a computer program which performs every step of the method and to a machine-readable storage medium which stores the computer program. The invention finally relates to an electronic control unit adapted for performing the method.

An SCR catalyst (selective catalytic reduction) may be used to reduce nitrogen oxide emissions in the exhaust gas of internal combustion engines, in particular of diesel engines. An ammonia-eliminating reagent such as for example aqueous urea solution (urea-water solution UWS) is metered in upstream of the SCR catalyst. In the SCR catalyst the ammonia then undergoes catalytic reaction with the nitrogen oxides containing primarily nitrogen monoxide and nitrogen dioxide to form nitrogen and water vapor. A nitrogen oxide sensor may be used to monitor the concentration of unconverted nitrogen oxides downstream of the SCR catalyst.

Conventional nitrogen oxide sensors have a similar sensitivity towards nitrogen monoxide and nitrogen dioxide. They are also sensitive to ammonia, and the sensitivity towards ammonia substantially corresponds to the sensitivity towards nitrogen monoxide and nitrogen dioxide. A nitrogen oxide sensor arranged downstream of an SCR catalyst therefore provides an aggregate signal of unconverted nitrogen oxides and ammonia that was either not consumed during the SCR reaction or is released by a desorption in the SCR catalyst.

DE 10 2010 028 543 A1 describes a mixed potential sensor which makes it possible to undertake not only a selective ammonia measurement but also a selective measurement of nitrogen oxides. Said sensor comprises a mixed potential electrode, i.e. an electrode comprising an electrode material which ensures that the electrode no longer behaves like an equilibrium electrode but rather exhibits an electrode potential determined by the kinetics of the electrode reaction. The use of two mixed potential electrodes on a common sensor element allows simultaneous and selective determination of two different gas components in one gas sensor, for example the determination of ammonia and nitrogen dioxide. The oxygen concentration in the exhaust gas must likewise be measured since the mixed potential depends on the particular oxygen content of the environment.

SUMMARY OF THE INVENTION

The method is used for monitoring a gas sensor which comprises a plurality of electrochemical measuring cells, in particular two measuring cells, and which is arranged in an exhaust tract of an internal combustion engine, in particular downstream of the SCR catalyst. The measuring cells exhibit a substantially identical sensitivity towards a first gas component, for example ammonia, and a different sensitivity towards a second gas component, for example nitrogen dioxide. Sensitivity is to be understood as meaning a sensitivity obtained after raw values from the measuring cells have been subjected to a calibration. Said cells are in particular insensitive towards further gas components, for example nitrogen monoxide or hydrocarbons. Such a gas sensor may be realized in particular by using two mixed potential electrodes that each have a different chemical composition, this leading to different but known sensitivities towards the second gas component. Since such a gas sensor provides two mixed potentials these two electrical voltages may be used to calculate both the concentration of the first gas component present in an exhaust gas and the concentration of the second gas component. The respective signals are thus already resolved by the cross-influence of the respective other gas. The method thus makes it possible to detect when one of the measuring cells of the gas sensor has a defect.

To this end, in an operating state in which an exhaust gas stream in the gas sensor contains less of the second gas component than of the first gas component a concentration of the first gas component is calculated from each of the sensor signals from the mixed potential electrodes. A defect in a measuring cell is deduced from the concentrations of the first gas component. What is made use of here is that substantially identical sensor signals are to be expected when both sensor signals are determined substantially only by the content of the first gas component of the exhaust gas. A deviation from this expected behavior may be utilized to detect that one of the measuring cells has a defect.

A simple method for determining the defect is that of deducing a defect when a difference in the concentrations of the first gas component exceeds a threshold value.

In one exemplary embodiment of the method the exhaust gas contains not only the first gas component but also the second gas component, although the concentration of the second gas component in the exhaust gas is lower than the concentration of the first gas component. If the difference between the concentration of the first gas component and the concentration of the second gas component is sufficiently large however, the different influence of the second gas component on the two sensor signals can be neglected and a concentration of the first gas component may be calculated from each sensor signal. If the two concentrations of the first gas component then differ by more than a predeterminable threshold value for example, a defect in a measuring cell may be assumed.

In another embodiment of the method the exhaust gas contains no second gas component in the operating state. This allows direct calculation of a concentration of the first gas component from each of the two sensor signals. Comparison of the difference in concentrations of the first gas component with the threshold value in particular then allows a defect in the measuring cell to be diagnosed.

Yet another embodiment of the method may be employed in an operating state in which the exhaust gas contains no nitrogen monoxide and no nitrogen dioxide when the first gas component is ammonia and the second gas component is nitrogen dioxide. An ammonia concentration is then deduced in the gas sensor from an amperometric signal from a nitrogen oxide cell of the gas sensor which may also be present in the gas sensor in addition to the two mixed potential electrodes and an oxygen measuring cell. To this end, the ammonia sensitivity of the nitrogen oxide cell including its oxygen dependence and its concentration dependence should be known. Each of the two ammonia concentrations from the two measuring cells is then compared with the ammonia concentration calculated from the amperometric signal. If the difference between this ammonia concentration and one of the ammonia concentrations from the measuring cells exceeds a threshold value a defect in the respective measuring cell is deduced. While the embodiments of the method described hereinabove merely make it possible to deduce a defect in one of the sensor elements without being able to determine which of the elements is defective, this embodiment of the method allows for pinpointing of the defective measuring cell.

An operating state suitable for performing the method is in particular a coasting operation of the internal combustion engine in which no fuel is burned and thus no nitrogen oxides are generated either.

Another suitable operating state for performing the method is present in particular when an efficiency of the SCR catalyst exceeds a threshold value. This threshold value may be chosen such that no nitrogen oxides are to be expected downstream of the SCR catalyst or such that the concentration thereof is expected to be low compared to the ammonia concentration downstream of the SCR catalyst.

The computer program is adapted for performing each step of the method, in particular when it is run on a computer or an electronic control unit. It allows implementation of different embodiments of the method on an electronic control unit without the need to make structural alterations thereto. To this end it is stored on the machine-readable storage medium.

Installing the computer program on a conventional electronic control unit affords the electronic control unit adapted for monitoring a gas sensor by means of the method.

DETAILED DESCRIPTION

Figure 1:
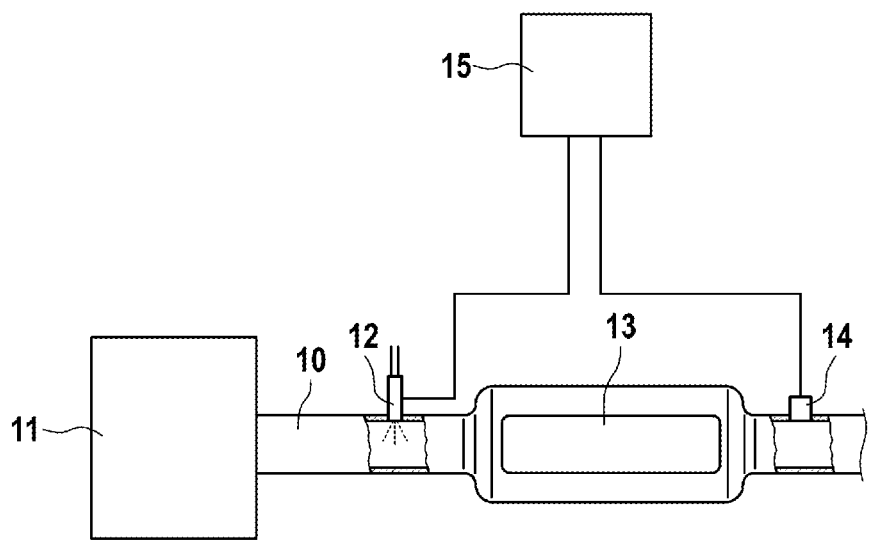
FIG. 1 is a schematic diagram of an exhaust tract having arranged in it a gas sensor that may be monitored by means of exemplary embodiments of the method according to the invention.

An exhaust tract 10 of an internal combustion engine 11 is shown in FIG. 1. Therein, a metering unit 12 is arranged downstream of an SCR catalyst 13. It allows metered addition of UWS into the exhaust tract 10. Said solution eliminates ammonia which reacts with nitrogen oxides from the exhaust gas of the internal combustion engine 11 to afford nitrogen and water vapor in an SCR reaction in the SCR catalyst 13. Arranged downstream of the SCR catalyst 13 in the exhaust tract is a gas sensor 14. This provides measured data to an electronic control unit 15 of the internal combustion engine 11 which also controls the metering unit 12.

Figure 2:
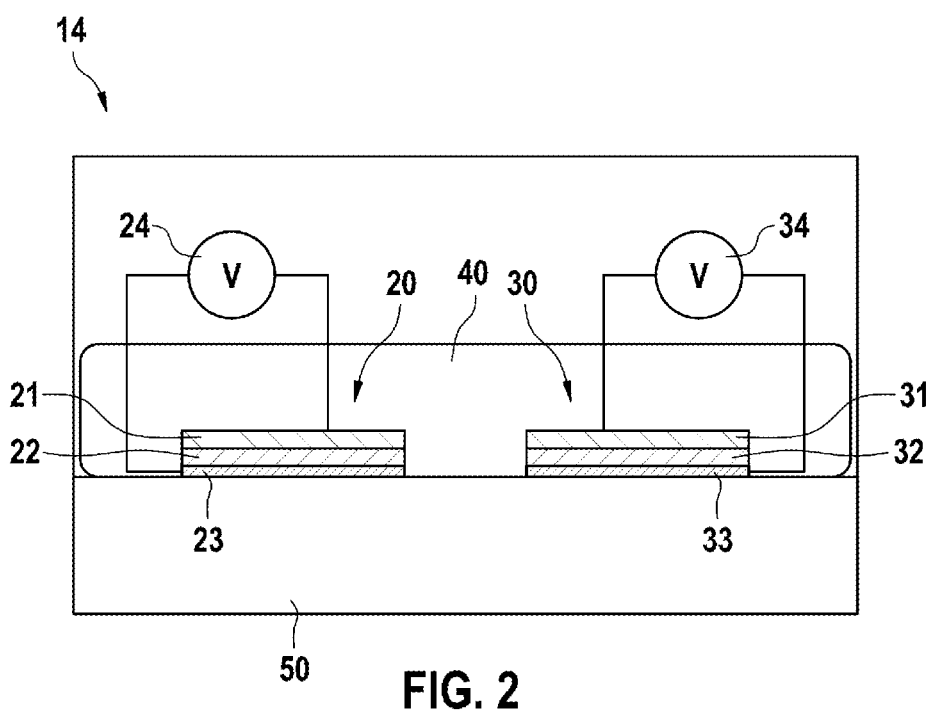
FIG. 2 is a schematic diagram of important elements of a gas sensor that may be monitored by means of exemplary embodiments of the method according to the invention.

FIG. 2 shows details of the gas sensor 14. Said sensor comprises a first electrochemical measuring cell 20 and a second electrochemical measuring cell 30. The first measuring cell 20 comprises a mixed potential electrode 21 which is separated by a solid electrolyte 22 from a reference electrode 23. The electromotive force (EMF) between the mixed potential electrode 22 and the reference electrode 24 is measured as the first sensor signal $S_{20}$ by a voltage measuring means 24. The second measuring cell 30 is analogously made up of a mixed potential electrode 31, a solid electrolyte 32, a reference electrode 33 and a voltage measuring means 34. It provides a second sensor signal $S_{30}$. While the solid electrolyte 22, 23 in both sensor elements is identical and in the present case may be for example an oxygen ion conductor such as yttria-stabilized zirconia (YSZ), the two mixed potential electrodes 21, 22 have different compositions. For example these two mixed potential electrodes 21, 22 may be platinum electrodes having different proportions of gold alloyed with them. The measuring cells 20, 30 are surrounded by a protective layer 40. In order to measure an aggregate signal of ammonia, nitrogen monoxide and nitrogen dioxide the gas sensor 14 further comprises an amperometric nitrogen oxide sensor 50 comprising a plurality of measuring cells (not shown), a heater and protective layers.

Figure 3:
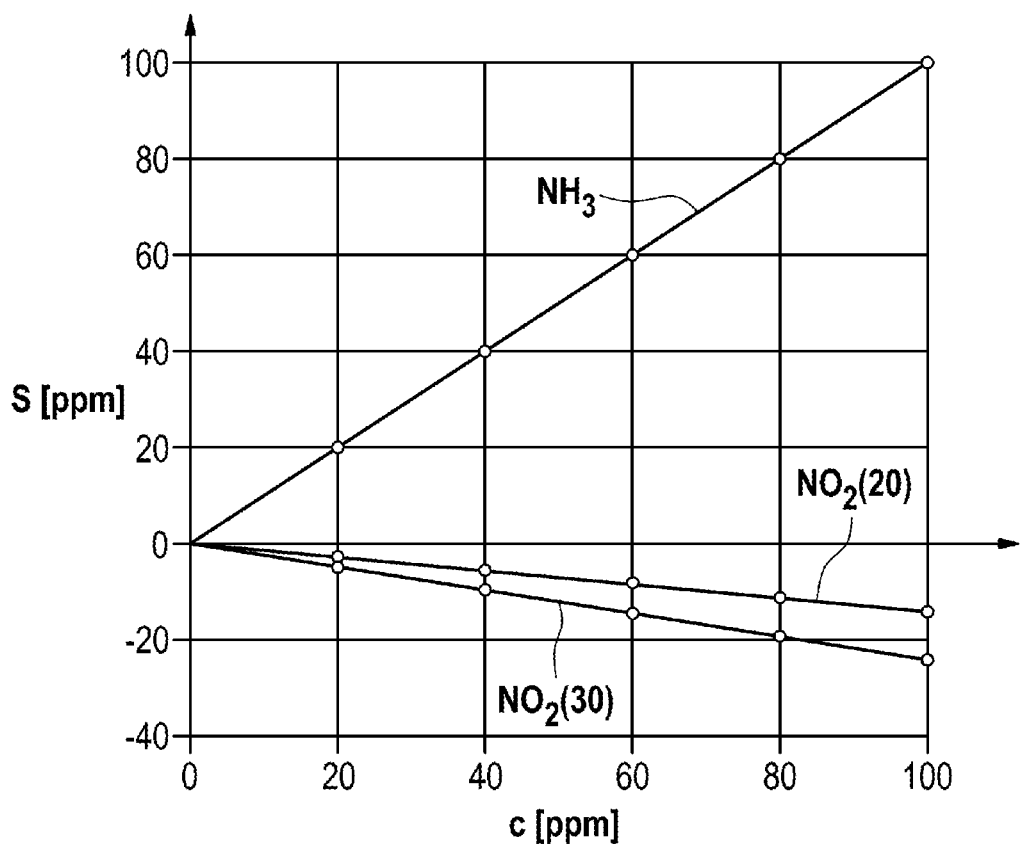
FIG. 3 diagramatically shows the dependence of sensor signals from measuring cells in a gas sensor that may be monitored by means of exemplary embodiments of the method according to the invention on the concentrations of ammonia, nitrogen monoxide and nitrogen dioxide in an exhaust gas.

While the nitrogen oxide sensor 50 has the same sensitivity for ammonia, nitrogen monoxide and nitrogen dioxide and provides an aggregate signal of the concentration of these three gases in the exhaust gas the two measuring cells 20, 30 each have different sensitivities for these gases. Calibration makes it possible to obtain from the raw signals from the measuring cells 20, 30, which are dependent not only on the ammonia concentration but also on the oxygen concentration of the atmosphere, the mixed potentials of a corresponding ammonia concentration and nitrogen dioxide concentration. Such a calibration results, as shown in FIG. 3, in a linear correlation between the concentration c of ammonia $NH_3$ in the exhaust gas and its sensor signal S. In the absence of other gases to which the two measuring cells 20 and 30 are sensitive an ammonia concentration of for example 100 ppm results in sensor signals S of 100 ppm in each case. The two measuring cells 20, 30 are insensitive to nitrogen monoxide NO. The presence of nitrogen dioxide $NO_2$ results in a sensor signal opposed to the ammonia signal so that a nitrogen dioxide concentration of 100 ppm in the absence of ammonia in the exhaust gas results in a sensor signal S from the first measuring cell 20 of −20 ppm. After appropriate calibration of its sensitivity towards ammonia and nitrogen monoxide the further sensor signal S of the second measuring cell 30 is equal to the signal S of the first measuring cell 20. However, the sensitivity towards nitrogen dioxide for the sensor signal S from the second measuring cell 30 is higher compared to the sensor signal S from the first measuring cell 20. In the second measuring cell 30 the presence of 100 ppm of nitrogen dioxide without ammonia results in a signal of −40 ppm. Since the insensitivity of both measuring cells 20, 30 towards nitrogen monoxide means that only two parameters, namely the ammonia concentration and the nitrogen dioxide concentration, are unknown and two sensor signals S are available for calculation thereof, both the ammonia concentration and the nitrogen dioxide concentration can be calculated in the gas sensor 14. As soon as the ammonia concentration and the nitrogen dioxide concentration are available from this calculation the nitrogen monoxide concentration can also be determined using the aggregate signal resulting from the amperometric NOx signal from the nitrogen oxide sensor 50 knowing the ammonia and nitrogen dioxide sensitivities of the NOx cell and accounting for the oxygen concentration and the gas concentration.

The gas sensor 14 may be monitored in different exemplary embodiments of the method according to the invention. A first exemplary embodiment of the method may be employed in an operating state in which the ammonia concentration downstream of the SCR catalyst 13 is markedly higher than the nitrogen dioxide concentration. This is the case for example when due to a high ammonia fill level of the SCR catalyst 13 and on account of a high temperature the efficiency of the SCR reaction is poor and desorption of ammonia, and thus ammonia slip, occur. In this operating state the contribution of the nitrogen dioxide to the two sensor signals S may be neglected to a good approximation and it may be assumed that both measuring cells 20, 30 are showing only the ammonia content of the exhaust gas. If the two sensor signals S differ by more than a threshold value, chosen to account for the fact that the nitrogen dioxide present in small amounts may result in differences between the two sensor signals S, it must be assumed that at least one of the two measuring cells 20, 30 is defective and an error is logged in the electronic control unit 15.

In a second exemplary embodiment of the method according to the invention the exhaust gas contains no nitrogen dioxide downstream of the SCR catalyst 13. This may be achieved for example in an operating state in which an oxygen-poor combustion process at most permits the formation of nitrogen monoxide. In this exemplary embodiment it is also assumed that both sensor signals S each show the ammonia concentration in the exhaust gas downstream of the SCR catalyst 13. If they differ from one another by more than a threshold value then here too a defect of at least one of the two measuring cells 20, 30 is assumed. Since there is no disruptive influence from the presence of nitrogen dioxide this threshold value may be lower than in the first exemplary embodiment of the method.

A third exemplary embodiment of the method may be employed in an operating state in which the exhaust gas contains no nitrogen oxides whatsoever. Such an operating state is present for example in a coasting operation of the internal combustion engine 11. Both the sensor signals S from the two measuring cells 20, 30 and the signal from the amperometric aggregate signal in this operating state correspond to the ammonia concentration downstream of the SCR catalyst 13. If the ammonia concentration determined by means of one of the measuring cells 20, 30 differs from that according to the nitrogen oxide sensor 50 it is assumed that the mixed potential cell having the deviating ammonia concentration is defective. If, by contrast, the ammonia concentrations from both measuring cells 20, 30 differ from that from the nitrogen oxide sensor 50 but are identical to one another, a defect in the nitrogen oxide sensor 50 may be deduced.

The invention claimed is:

1. A method for monitoring a gas sensor (14) which comprises at least two electrochemical measuring cells (20, 30) and which is arranged in an exhaust tract (10) of an internal combustion engine (11), wherein the measuring cells (20, 30) exhibit a substantially identical sensitivity to a first gas component and a different sensitivity to a second gas component and are insensitive to other gas components, the method comprising:
   determining, in a first operating state in which an exhaust gas stream at the gas sensor (14) contains less of the second gas component than of the first gas component, a concentration of the first gas component from each of the sensor signals (S) from the measuring cells (20, 30), and
   determining a defect in a measuring cell (20, 30) from a comparison of the determined concentration of the first gas component for each measuring cell (20, 30).

2. The method according to claim 1, wherein the gas sensor (14) is arranged downstream of an SCR catalyst (13), the first gas component is ammonia (NH3) and the second gas component is nitrogen dioxide (NO2).

3. The method according to claim 1, wherein a defect is deduced when a difference in the calculated concentrations of the first gas component exceeds a threshold value.

4. The method according to claim 1, wherein the exhaust gas contains no second gas component in the operating state.

5. The method according to claim 2, wherein in second operating state in which the exhaust gas contains no nitrogen monoxide (NO) and no nitrogen dioxide (NO2) an ammonia concentration in the gas sensor (14) is determined from a signal from a nitrogen oxide sensor (50) of the gas sensor (14) and a defect is determined when a difference between this ammonia concentration and one of the calculated ammonia concentrations exceeds a threshold value.

6. The method according to claim 1, wherein the operating state is a coasting operation of the internal combustion engine (10).

7. The method according to claim 1, wherein an efficiency of the SCR catalyst (13) exceeds a threshold value in the operating state.

8. A computer-readable storage medium containing instructions that when executed by a computer cause the computer to monitor a gas sensor (14) which comprises at least two electrochemical measuring cells (20, 30) and which is arranged in an exhaust tract (10) of an internal combustion engine (11), wherein the measuring cells (20, 30) exhibit a substantially identical sensitivity to a first gas component and a different sensitivity to a second gas component and are insensitive to other gas components, by:
   determining, in a first operating state in which an exhaust gas stream at the gas sensor (14) contains less of the second gas component than of the first gas component, a concentration of the first gas component from each of the sensor signals (S) from the measuring cells (20, 30), and
   determining a defect in a measuring cell (20, 30) from a comparison of the determined concentration of the first gas component for each measuring cell (20, 30).

9. An electronic control unit (15) adapted for monitoring a gas sensor (14) by means of a method according to claim 1.

* * * * *